US00PP26719P3

(12) United States Plant Patent
Miller

(10) Patent No.: US PP26,719 P3
(45) Date of Patent: May 10, 2016

(54) ***IPOMOEA* PLANT NAMED 'DAYBREAK'**

(50) Latin Name: ***Ipomoea indicia* var. *acuminata***
Varietal Denomination: DAYBREAK

(71) Applicant: Luen Miller, Santa Cruz, CA (US)

(72) Inventor: Luen Miller, Santa Cruz, CA (US)

( * ) Notice: Subject to any disclaimer, the term of this patent is extended or adjusted under 35 U.S.C. 154(b) by 113 days.

(21) Appl. No.: 14/120,394

(22) Filed: May 16, 2014

(65) Prior Publication Data

US 2015/0334893 P1 Nov. 19, 2015

(51) Int. Cl.
*A01H 5/02* (2006.01)

(52) U.S. Cl.
USPC ..... Plt./263.1

(58) Field of Classification Search
USPC ..... Plt./226, 263.1
See application file for complete search history.

*Primary Examiner* — Susan McCormick Ewoldt
(74) *Attorney, Agent, or Firm* — Cassandra Bright

(57) ABSTRACT

A new and distinct *Ipomoea indica* var. *acuminata* cultivar named 'DAYBREAK' is disclosed, characterized by yellow-green foliage. The new cultivar is an *Ipomoea indica* var. *acuminata*, typically suited for ornamental container and garden use.

4 Drawing Sheets

Latin name of the genus and species: *Ipomoea indica* var. *acuminata*.
Variety denomination: 'DAYBREAK'.

BACKGROUND OF THE INVENTION

The new variety originated as a chance discover by the inventor, Luen Miller. The variety was discovered as a naturally occurring whole plant mutation among a planting of unpatented, unnamed *Ipomoea indica* var. *acuminata*. The new variety was discovered during the Summer of 2000 at a commercial nursery in Royal Oaks, Calif.

After selecting and isolating the new cultivar, asexual reproduction of the new cultivar 'DAYBREAK' was first performed at the same commercial nursery in Royal Oaks, Calif. Vegetative terminal cuttings were used for propagation. The inventor continued confidential, controlled evaluation and propagation of 'DAYBREAK', to establish a stable clone, with the most yellow-green foliage coloration. 'DAYBREAK' has since produced several generations and has shown that the unique features of this cultivar are stable and reproduced true to type. Typical asexual reproduction of the new variety is by vegetative cuttings.

SUMMARY OF THE INVENTION

The cultivar 'DAYBREAK' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DAYBREAK'. These characteristics in combination distinguish 'DAYBREAK' as a new and distinct *Ipomoea* cultivar:

1. Distinctive Yellow-Green foliage, especially on younger foliage.
2. Mature foliage maintains Yellow-Green Coloration in full sun situations.

PARENTAL COMPARISON

Plants of the new cultivar 'DAYBREAK' are similar to the parent in most horticultural characteristics. However, 'DAYBREAK' differs in producing foliage distinctive colored Yellow-Green when immature and in full sun. The parent variety has green foliage. Additionally, plants of the new variety are less vigorous than plants of the parent variety.

COMMERCIAL COMPARISON

Plants of the new cultivar 'DAYBREAK' can be compared to the well-known commercial variety *Ipomoea batatas* 'Marguerite', unpatented. Plants of 'DAYBREAK' are similar to plants of 'Marguerite' in some horticultural characteristics, however, plants of 'DAYBREAK' form a very long, twining plant, with abundant flowering. 'Marguerite' does not typically flower, and forms a mounding, trailing plant.

Plants of the new cultivar 'DAYBREAK' can be compared to *Ipomoea marginata*. The new variety is similar in some horticultural characteristics. However, the plants of 'DAYBREAK' are less vigorous, and produce a violet-blue flower, compared to the white flower of this comparator. Additionally, foliage the new variety can be yellow-green whereas *Ipomoea marginata* always produces green foliage.

BRIEF DESCRIPTION OF THE PHOTOGRAPHS

The accompanying photographs were taken using conventional techniques and although colors may appear different from actual colors due to light reflectance it is as accurate as possible by conventional photographic techniques.

Figure 1:
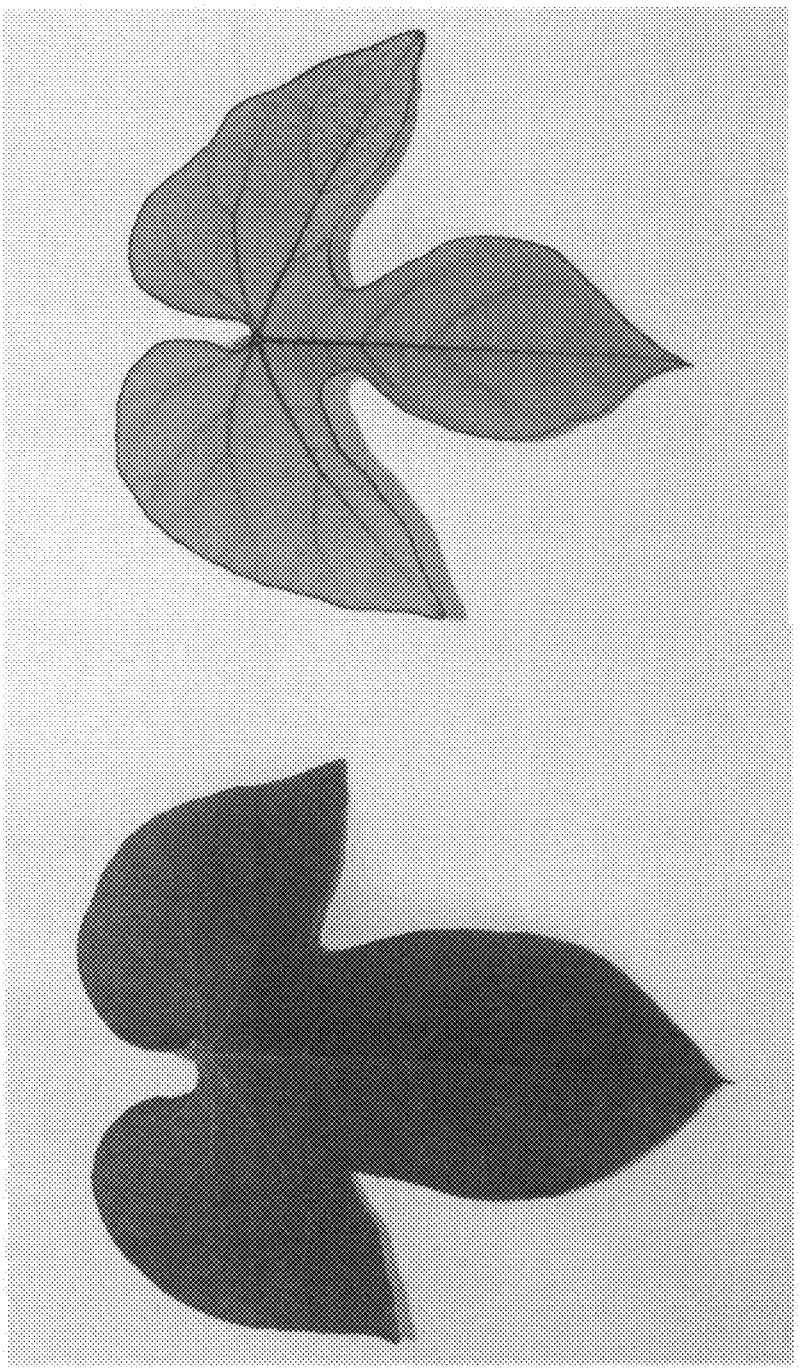
FIG. 1 illustrates in full color a comparison of young foliage of the commercially known species *Ipomoea indica* var. *acuminata* with typical young foliage of the new variety 'DAYBREAK'. Foliage of 'DAYBREAK' is the yellow-green leaf on the right side of the photograph.
Figure 2:
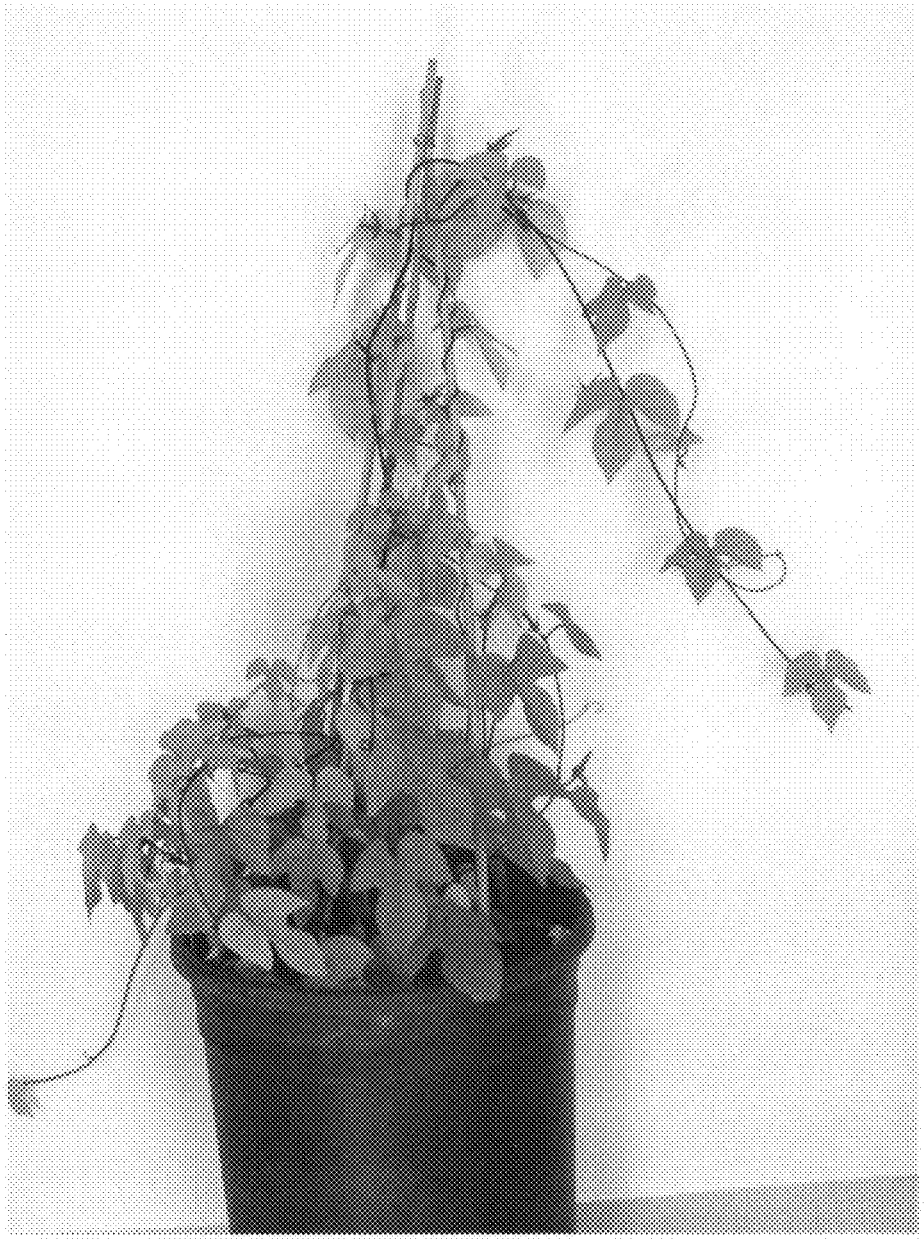
FIG. 2 illustrates a typical plant of 'DAYBREAK' grown outdoors in Royal Oaks, Calif. This plant is approximately 20 weeks old, from an unrooted cutting.
Figure 3:
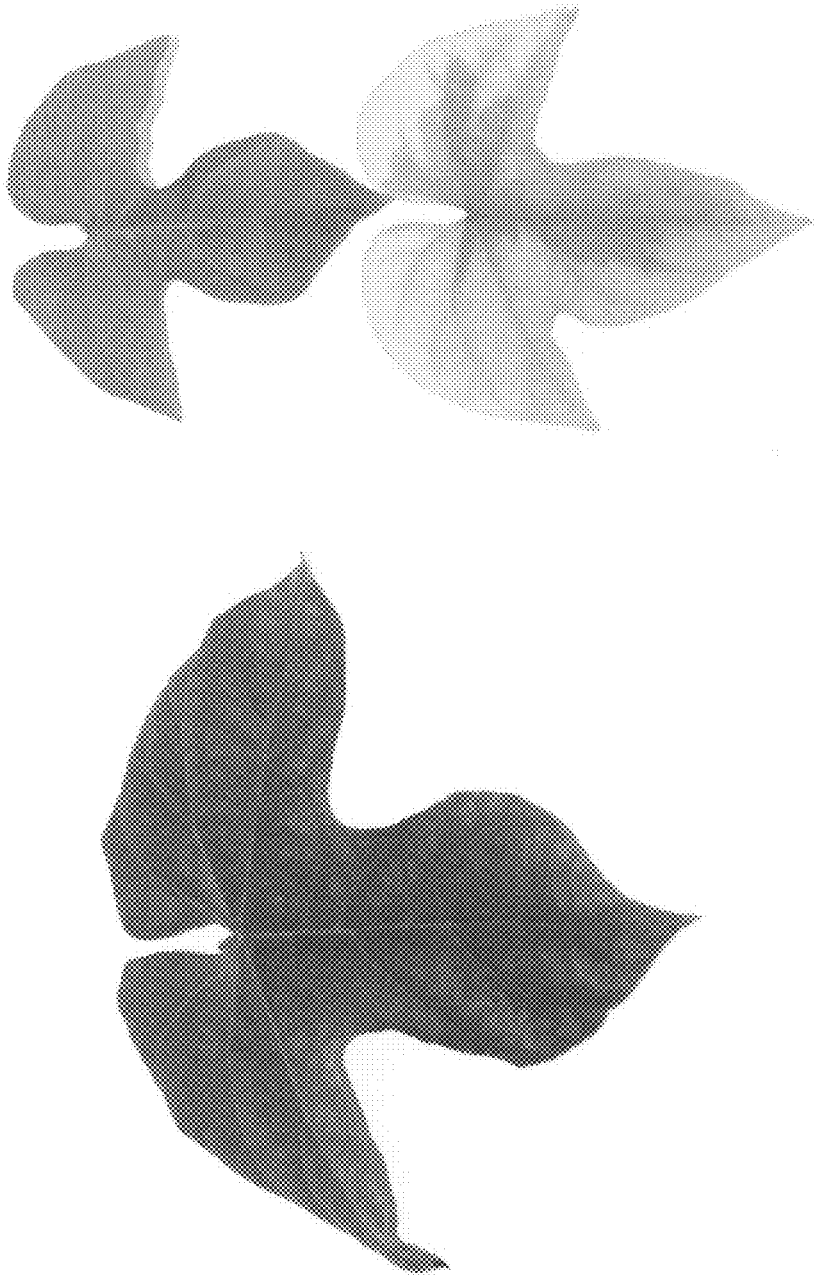

FIG. 3 illustrates in full color a comparison of mature foliage of the commercially known *Ipomoea indica* var. *acuminata* with typical mature foliage of the new variety 'DAYBREAK'. Foliage of 'DAYBREAK' is the yellow-green mottled leaf on the right side of the photograph, and the light green leaf also found on the right side of the photograph. Both are typical examples of mature foliage found on 'DAYBREAK'.

Figure 4:
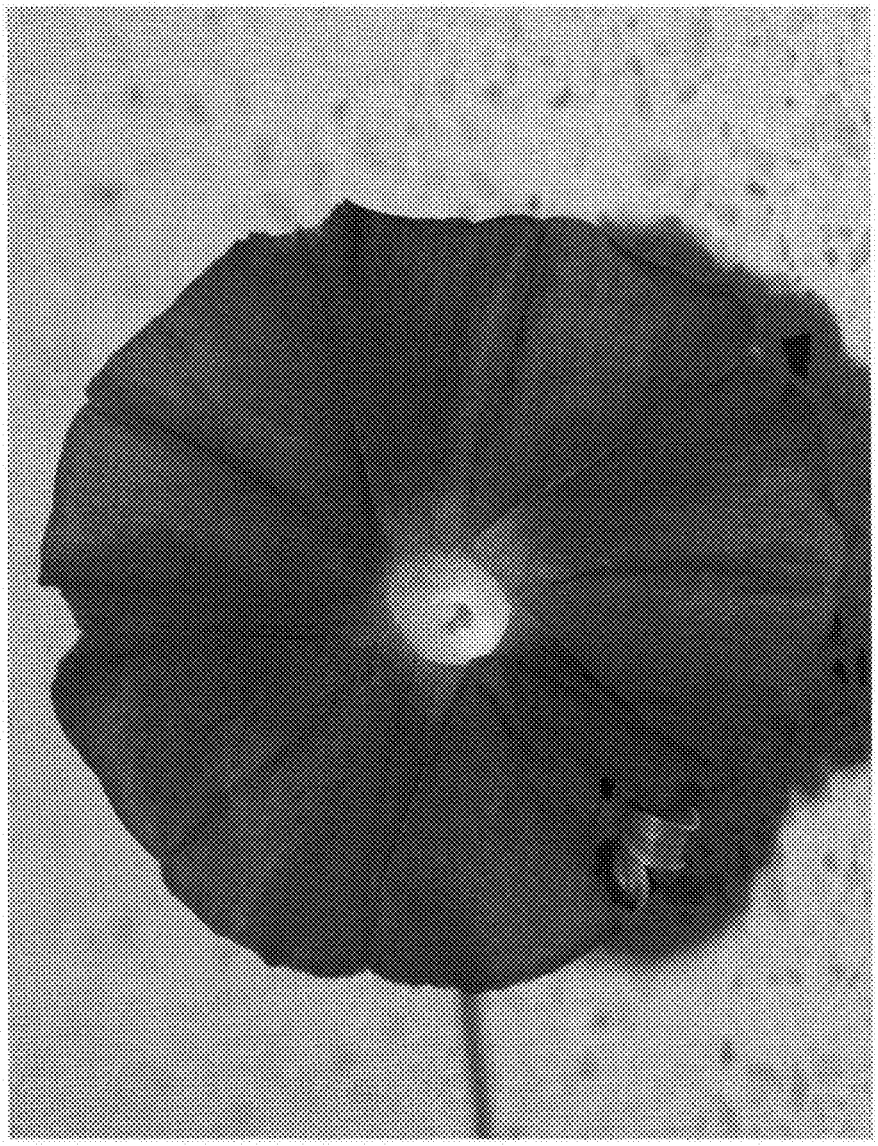

FIG. 4 illustrates in full color a typical flower of 'DAYBREAK'.

DETAILED BOTANICAL DESCRIPTION

In the following description, color references are made to The R.H.S. Colour Chart, 2007, except where general terms of ordinary dictionary significance are used. The following observations and measurements describe 'DAYBREAK' plants grown during the Spring months in a greenhouse in Oxnard, Calif., under bright, unshaded conditions. Average day temperatures were approximately 20° C. to 26° C. and the average night temperature was approximately 15° C. to 18° C. No artificial light, photoperiodic treatments or chemical treatments were given to the plants. Measurements and numerical values represent averages of typical plant types.

Botanical classification: *Ipomoea indica* var. *acuminata* 'DAYBREAK'.

Age of the plant described: Approximately 20 weeks from an unrooted cutting.

Container size of the plant described: 5 gallon commercial container.

PROPAGATION

*Propagation method*.—Terminal cuttings.

*Time to develop roots suitable for transplanting*.—Summer about 6 days at an average temperature of 24° C.; Winter-about 10 days at an average temperature of 24° C.

*Root description*.—Fibrous.

*Tuber description*.—None observed.

PLANT

*Growth habit*.—Twining vine. Can also creep along ground if unsupported.

*Height*.—Measured from top of soil line of pot, approximately 60 cm, with a stake in the pot for the vine to grow up.

*Plant spread*.—Approximately 45 cm.

*Growth rate*.—Rapid.

*Branching characteristics*.—Not very free branching unless pinched. Will produce lateral branches from any node from a pinch.

Primary branches:

*Length*.—A range between 80 to 150 cm on a 1 year old plant.

*Diameter*.—Approximately 0.3 cm.

*Texture*.—Pubescent.

*Color*.—Most commonly near RHS Greyed-Purple N187A.

*Strength*.—Very flexible, young growth easily broken, older growth becomes stiff and strong like twine.

*Internode length*.—Average range between 5 cm to 15 cm.

*Adventitious roots at nodes*.—Not observed.

New shoot growth characteristics:

*Color*.—Near Greyed-Orange 165A.

*Aspect*.—Twining.

*Texture*.—Highly pubescent. Hairs colored near Orange-White 159D, approximately 0.15 cm long.

FOLIAGE

Leaf:

*Arrangement*.—Alternate, simple.

*Average length*.—9 cm.

*Average width*.—8 cm.

*Shape of blade*.—3 lobed or more rarely, cordate.

*Apex*.—Acute.

*Base*.—Cordate.

*Margin*.—Entire.

*Aspect*.—Very slight upward fold and slight undulation occasionally.

*Texture of top surface*.—Pubescent, velvety.

*Texture of bottom surface*.—Pubescent.

*Quantity of leaves per lateral branch*.—Average 10 to 18 on a 100 cm length of stem.

Foliage color:

*Young foliage upper side*.—Typically near RHS Yellow-Green N144A, variegated or flushed with Yellow-Green 151C. Leaves can be solid colored with flushing, or variegated.

*Young foliage under side*.—Near RHS Yellow-Green 146D.

*Mature foliage upper side*.—Typically near RHS Yellow-Green N144C, solid colored with flushing, or variegation of Yellow-Green N144A. Foliage can also be colored Yellow-Green 144A. Margins can have a very fine line of Greyed-Purple 187A.

*Mature foliage under side*.—Near RHS Yellow-Green 144B.

Venation:

*Type*.—Reticulate.

*Venation color upper side*.—Near Greyed-Purple 187A, or Yellow-Green 144B, flushed 187A, or Yellow-Green 144B.

*Venation color under side*.—Near Yellow-Green 146D.

Petiole:

*Length*.—Average range from approximately 2.0 to 4.5 cm.

*Diameter*.—Approximately 0.2 cm.

*Texture*.—Highly pubescent. Hairs colored near Yellow-Green 145D.

*Color*.—Near Greyed-Purple N187A.

*Strength*.—Strong.

*Aspect*.—Straight to slightly curved.

FLOWER

Natural flowering season: Flowering begins in April or early May.

Inflorescence and flower type and habit: Axillary, solitary salverform single flowers.

Rate of flower opening: About 5 days from bud to fully opened flower.

Flower longevity on plant: About 2 to 3 days.

Persistent or self-cleaning: Self-Cleaning.

Bud:

*Shape*.—Oblong.

*Length*.—About 5.8 cm.

*Diameter*.—About 1.7 cm.

*Color*.—RHS Purple 78C.

Flower size:
*Diameter*.—Average 5.6 cm.
*Length*.—Average 6.5 cm.
*Corolla tube diameter*.—About 1.4 cm.
Corolla/petals:
*Arrangement*.—Symmetric.
*Lobe length*.—About 1.0 cm.
*Lobe width*.—About 2.5 cm.
*Quantity*.—5.
*Texture*.—Velvety.
*Lobe apex*.—Mucronate.
*Margin*.—Entire.
Color:
*When opening*.—Upper surface: RHS Violet-Blue N89B, faint, star shaped pattern, at fusion of lobes, colored near Purple 77A. Lower surface: RHS Violet-Blue N89D, star shaped pattern colored near Purple 76A.
*Fully opened*.—Upper surface: RHS Violet-Blue N89C, faint, star shaped pattern, at fusion of lobes, colored near Purple-Violet N81A. Lower surface: RHS Violet-Blue N89B, star shaped pattern colored near Purple 76A.
Corolla tube:
*Length*.—Average 3.5 cm.
*Diameter*.—Widest point average 1.5 cm, narrowest, average 1.0 cm.
*Texture*.—Glabrous all surfaces.
*Color*.—Inner Surface: Near RHS Violet 84C. Outer Surface: Near RHS Purple 75C and 75D.
Calyx/sepals:
*Quantity per flower*.—5, fused at approximately 50% from base.
*Shape*.—Narrow deltoid.
*Length*.—Average 2.4 cm.
*Width*.—About 0.6 cm, unfused individual sepal.
*Apex*.—Acute.
*Base*.—Fused.
*Margin*.—Entire.
*Texture*.—Slightly velvety exterior surfaces, glabrous interior.
*Color*.—Exterior Surface: Near RHS Yellow-Green 145C, apex near 144A. Interior Surface: RHS Yellow-Green 144A.
Peduncle:
*Length*.—Average 2.2 cm.
*Diameter*.—Approximately 0.2 cm.
*Color*.—Near RHS Greyed-Orange 177A.
*Orientation*.—Slanted upward and undulating.
*Pubescence*.—Slightly pubescent.
Fragrance: None.

REPRODUCTIVE ORGANS

Stamens:
*Number*.—5.
*Filament length*.—Approximately 1 cm.
Anthers:
*Shape*.—Flat, linear.
*Length*.—Approximately 0.5 cm.
*Color*.—Near RHS White 155A.
*Pollen*.—Color: Near RHS White 155A. Quantity: Moderate.
Pistil:
*Number*.—1.
*Length*.—About 3.2 cm.
*Style*.—Length: About 2.9 cm. Color: RHS White 155A.
*Stigma*.—Shape: Linear. Color: RHS White 155A. Ovary Color: RHS White 155A.

OTHER CHARACTERISTICS

Seeds and fruits: No seeds/fruits observed.
Disease/pest resistance: Neither resistance nor susceptibility to the normal pests and diseases of *Ipomoea* has been observed.
Temperature tolerance: Tolerates low temperatures to approximately 2° C. Good high temperature tolerance, observed to at least 40° C.

What is claimed is:

1. A new and distinct cultivar of *Ipomoea indica* var. *acuminata* plant named 'DAYBREAK' as herein illustrated and described.

* * * * *